June 25, 1963 L. F. CAYEUX Plant Pat. 2,266
HYDRANGEA PLANT
Filed Sept. 26, 1961
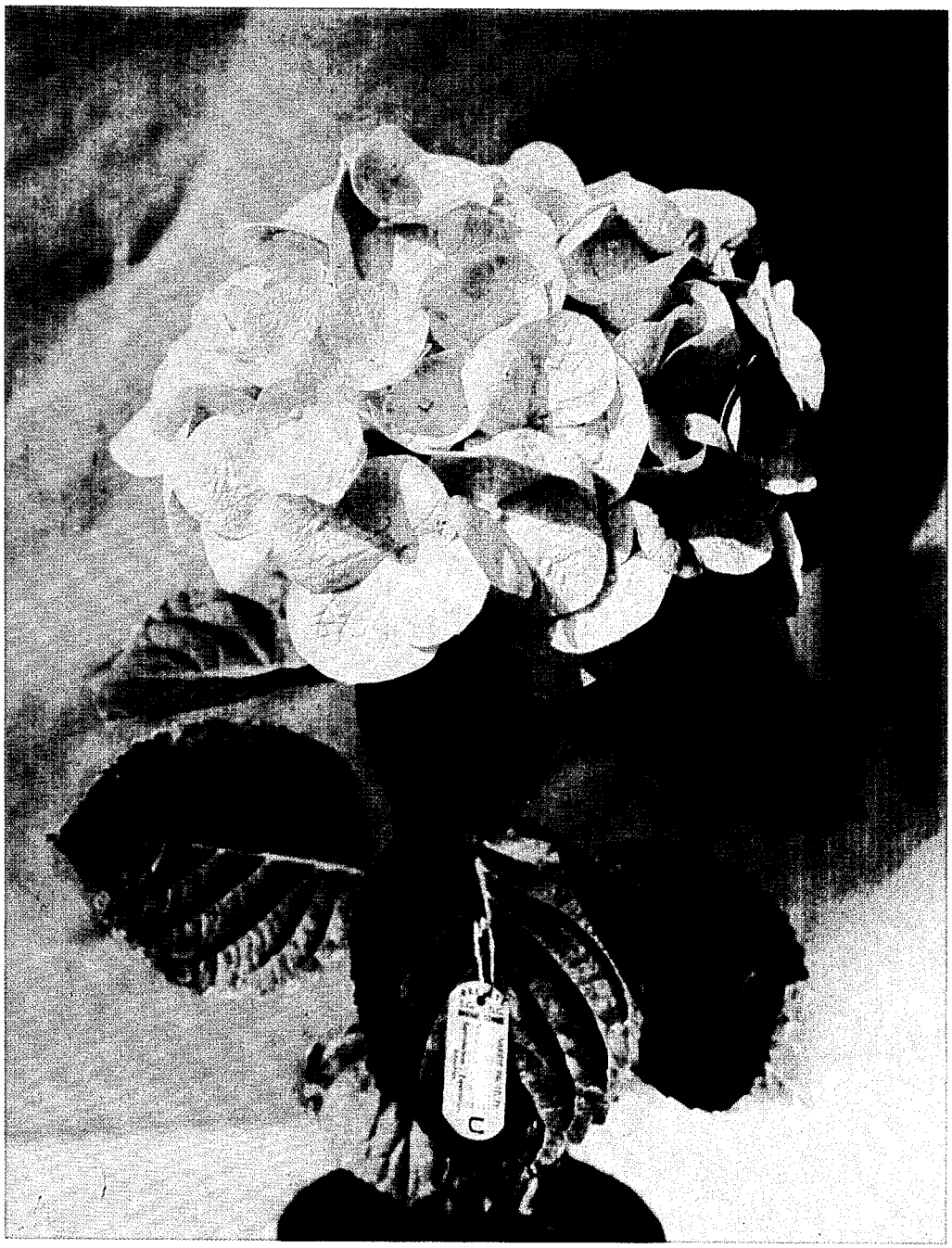
Inventor.
Louis Fernand Cayeux
By: Robb & Robb
Attorneys.

United States Patent Office

Plant Pat. 2,266
Patented June 25, 1963

2,266
HYDRANGEA PLANT

Louis Fernand Cayeux, Le Havre, France, assignor to Roger Talbot, Saint-Symphorien, Indre-et-Loire, France Filed Sept. 26, 1961, Ser. No. 140,963
Claims priority, application France Oct. 3, 1960
1 Claim. (Cl. Plt.—54)

The present invention relates to a new and distinct variety of hydrangea plant which was originated by me as a selected seedling derived by crossing two unnamed and unpatented hydrangea varieties respectively identified in my breeding records as hydrangea varieties No. 214 and No. 223, the former being the seed parent and the latter being the pollen parent.

The primary objective of this breeding was to produce a new hydrangea variety in which there is combined with the good characteristics of existing varieties, a new and distinct mauve-pink or lilac-pink flower color. This objective was fully achieved, along with other desirable features, as evidenced by the following unique combination of characteristics which are outstanding in the new variety and which distinguish it from its parents, as well as from all other varieties of which I am aware:

(1) Strong, stocky, and medium tall habits of growth;
(2) Thick, glossy green foliage;
(3) Relatively round leaves which are serrated along approximately ¾ of their upper edges;
(4) An early blooming habit;
(5) Well-formed flower buds of good keeping qualities;
(6) Flowerheads formed of florets having petaloid sepals (psuedo-sepals) of approximately diamond shape;
(7) A distinctive and attractive opaline lilac-pin general color tonality of the flowers, and the ability to easily take on a blue coloration;
(8) The ability to root readily from slips;
(9) Good weather and disease resistance; and
(10) Good indoor behavior of blooming plants.

Asexual reproduction of my new variety by slip rooting, as performed by me in France, shows that the foregoing characteristics and distinctions come true to form and are established and transmitted through succeeding propagations.

The accompanying drawing shows a typical specimen of the blooming plant of my new hydrangea variety, with the flowers and foliage depicted in color as nearly true as it is reasonably possible to make the same in a color illustration of this character.

The following is a detailed description of the new variety, with color terminology in accordance with Seguy's Universal Colour Code, published by Paul Lechevalier, of Paris, France, except where general color terms of ordinary dictionary significance are obvious:

Classification: hybrid hydrangea (hortensia).

*Plant*

Growth: After nipping off to obtain plants having several flowers, clusters from 3 to 10 branches fork from the base of the plant and attain a height of from 8 to 12 cm. in summer growth; lends itself quite well to early forcing; blooming occurs about 8 days earlier than existing varieties; very good budding ability, with quite satisfactory conservation of the flower buds in winter; very good rooting ability; very strong and quick growth; takes up blue coloration well. Nodes—spaced from 3 to 5 cm. apart; each branch bears from 4 to 6 pairs of leaves; buds form regularly in autumn and keep well in winter.

Flower stem: Strong; rigid; does not break easily; cylindrical cross-section; growth is green in color, with spots irregularly distributed and ranging from 2 to 3 mm. long and 1 to 2 mm. wide; spots correspond in color to color No. 111 and range in number from 1 to 5 or 6 per cm., but sometimes are completely absent on portions of the stem. Nodes—do not form a circular protuberance around the stem, but appear as bosses at the base of the axial bud and at the attachment point of the leaf petiole; distance between the 1st and 3rd nodes ranges from about 3 to 7 cm.; between the 3rd and 4th nodes distance ranges from about 4 to 6 cm.; and between the 4th and 6th nodes distance ranges from about 6 to 8 cm.

Leaves: Opposite; with petioles and serrations and an auxiliary bud at the foot of the petiole. Petiole—from 3 to 4 cm. long in full grown leaves; has a concave groove extending along its entire length and directed toward its upper face; complete, point-ended, serrated, glabrous limb of dark green color No. 416 on the upper side, and of light green color No. 357 on the lower side, said colors becoming lighter in the older leaves, and particularly those which are nearest to the starting point of the buds, which are as light as No. 372 on the upper side and No. 352 on the lower side; petiole extends to the tip of the leaf by the axial rib, with secondary ribs seldom starting from the same point on the axial rib, but with a fairly great number of small furrows starting from the secondary ribs and often running from one secondary rib to another; leaves are serrated only above their lower quarter, with wider spacing of the serrations toward the base of the leaf, and closer spacing toward the middle of the leaf, with maximum density of the serrations at the upper part of the leaf, ending in a triangular point, with the base of the point being fairly wide; full grown leaves are approximately round, while the leaves at the base of the flower stems and those under the flowerheads are slightly oval; parenchyma quite frequently does not begin on the petiole at the same height on both sides, but varies a few millimeters.

*Flowers*

Flowerheads (umbel): Terminal; composite; hemispherical; composed of florets varying in number from about 40 to 70 or more, with florets carried by a rigid peduncle having a length of from 2 to 4 cm.

Barren Flowers: Very numerous; composed of usually 4, but sometimes 5 or even 6 petaloid sepals having their free ends slightly notched, but having smooth edges and from 5 to 7 ribs (mostly 5) in a diverging arrangement, with the median rib being the most developed, and with secondary ribs extending from the latter and from the other radiating ribs; when in full bloom, the upper side of the pseudo-sepals often presents small bulges, and said pseudo-sepals are approximately of diamond shape, with their major axis ranging from 2.5 to 3.5 cm. long and their minor axis ranging from 2.5 to 4.5 cm. long; 4 additional small ovoid petals having a length of about 2 mm. and a width of about 2 mm. are combined with the pseudo-sepals aforementioned and have their edges tucked in toward the central portion of the flower, said small petals being of a violet color No. 13.

*Color.*—Color of pseudo-sepals is not uniform, and upper side is generally slightly darker at the starting point and slightly lighter toward the edge, and shading to color No. 54, while lower side ranges in color to color No. 49.

*Stamens.*—Usually 8 in number and having violet colored streaks.

*Pollen.*—Spherical grains.

*Ovaries.*—One inferior having one short style and 3 violet colored stigmas.

Fertile flowers: Scarce; calyx has 5 or sometimes 6 green sepals 2 mm. long and 2 mm. wide; corolla has 5 petals measuring 4 mm. by 2 mm., which are pink colored in the bud stage and violet colored, No. 618, in the full open stage; spherical pollen grains; gynoecium has one inferior ovary with 3 lobes; short style; 3 or sometimes 4 violet colored stigmas.

*Endurance*

Disease, pest and cold resistance: Very good resistance to ordinary diseases to which hydrangea plants are normally subject, but slightly sensitive to oidium when the weather is raw in summer or autumn; withstands the "anguillule" and normal winter frosts, all as determined by comparison with other hydrangea varieties grown under the same cultural conditions in France.

I claim:

A new and distinct variety of hydrangea plant, substantially as herein shown and described, characterized particularly as to novelty by the unique combination of strong, stocky and medium tall habits of growth, thick and glossy green foliage, relatively round leaves which are serrated along approximately ¾ of their upper edges, an early blooming habit, well formed flower buds of good keeping qualities, flower-heads formed of florets having petaloid sepals of approximately diamond shape, a distinctive and attractive opaline lilac-pink general color tonality of the flowers and the ability to easily take on a blue coloration, the ability to root readily from slips, good weather and disease resistance, and good indoor behavior of blooming plants.

No references cited.